United States Patent [19]

Imazio

[11] Patent Number: Plant 5,336

[45] Date of Patent: Nov. 13, 1984

[54] HEATHER NAMED ERICA SUNSET

[75] Inventor: Bruno L. Imazio, Watsonville, Calif.

[73] Assignee: Bruno Imazio Nursery, Watsonville, Calif.

[21] Appl. No.: 478,879

[22] Filed: Mar. 25, 1983

[51] Int. Cl.[3] ..... A01H 5/00

[52] U.S. Cl. ..... Plt./54

[58] Field of Search ..... Plt./54

*Primary Examiner*—Robert E. Bagwill

*Attorney, Agent, or Firm*—Chas. W. Rummler

[57] ABSTRACT

A new variety of heather particularly distinguished by its very early blooming habit relative to that of its parent and its profuse production of red-purple or magenta flowers which open progressively beginning with buds at the base of the stem and continuing rapidly to the tip of the stem. Whereas the parent does not begin to bloom until the end of February, this new plant begins to bloom early in December and continues through January well into February, its delightful deep and glowing color being advantageous for both the Christmas season and the Valentine's Day market.

2 Drawing Figures

BACKGROUND OF THE NEW PLANT

This new heather variety was discovered by me in 1978 as a seedling of unknown pollen parentage growing in a cultivated field of *Erica persoluta,* the variety believed to be the seed parent, where it was noticed because of its early blooming and particularly because of its reaching full bloom, from base to tip, more than a month before the parent plant begins to bloom. In general, this new plant resembles its seed parent, *persoluta,* in growth and flower color and its very early blooming habit is its distinctive character.

Since my discovery of this new plant I have reproduced it through successive generations by means of cuttings and have found that its early blooming habit remains true from generation to generation and appears to be firmly fixed.

DESCRIPTION OF THE DRAWINGS

This new heather variety is illustrated by the accompanying drawings which show, in the left hand view, the new plant in full bloom with a field of its seed parent just beginning to bud in the background, and at the right, a close-up of the plant showing the nature of its blossoms. The color shown is of a plant photographed on Dec. 8, 1982, at Watsonville, Calif.

DESCRIPTION OF THE NEW PLANT

The following is a detailed description of my new Heather Persoluta based upon observations of a field grown plant made in December 1982.

THE PLANT

Origin: Seedling.

Parentage: Seed parent — *Erica persoluta. Pollen parent — unknown.*

Classification: Botanic: *Erica persoluta 'Sunset'. Commercial: Sunset heather.*

Form: Woody shrub.

Shape: Generally upright, stems spreading to produce a fullness of the plant.

Height: From 2 to 3 feet.

Main stem length: About 20".

Branching: Generous. This plant is pruned back yearly to encourage branching.

Growth: Upright with woody and flexible strength.

Foliage: Abundant but with hardly visible, tiny, needle-like leaves over the entire plant.

Size of leaf: About ⅛ inch long.

Shape of leaf: Long and very narrow.

Color: Dark green.

In general, the foliage is too tiny to determine further characteristics by on-plant observation.

THE BUD

Size: Too tiny for accurate measure of size and shape.

Rate of opening: Rapid, progressive and continuous beginning at the base of the stem and progressing to the tip of the stem.

Petals: The bud has no separate petals or sepals.

Color: The buds are too tiny for accurate determination.

INFLORESCENCE

Blooming habit: Annual and profusely beginning in late fall—December.

Size of bloom: Very small with less than ⅛ inch in both diameter and depth.

Borne: In clusters.

Shape: Bell-shaped with pinched opening.

Texture: Soft.

Appearance: Satiny.

Color: Red-Purple or Magenta, R.H.S. 67D.

Flower stem: Stems supporting clusters of blooms.

*Length.*—From ¼ inch to 6 inches.

*Color.*—Light Brown.

*Strength.*—Supple, branching upwardly about 45° from main stem.

Discoloration after full bloom: Color bleaches out somewhat in the sun.

Effect of weather: Prolonged exposure to either wet or hot weather is detrimental.

Persistence: The blooms persist long after the stem ceases to draw water.

Fragrance: Mild, slightly sweet.

Lasting quality:

*On plant.*—2 To 3 months.

*As cut flower.*—3 Weeks.

The outstanding characteristic of this new plant resides in its blooming late in the fall to reach full maturity early in December and continuing through January and into February, whereas the parent plant does no begin to bloom until the very end of February. This early blooming habit of the new variety is an especially advantageous feature because the deep and glowing color has a tremendous market potential for the Christmas season, especially since there is no other heather with such a color available at that time.

I claim:

1. A new variety of *Heather persoluta*, substantially as herein shown and described, particularly characterized by its profuse production of blooms over the entire length of the stem beginning early in December.

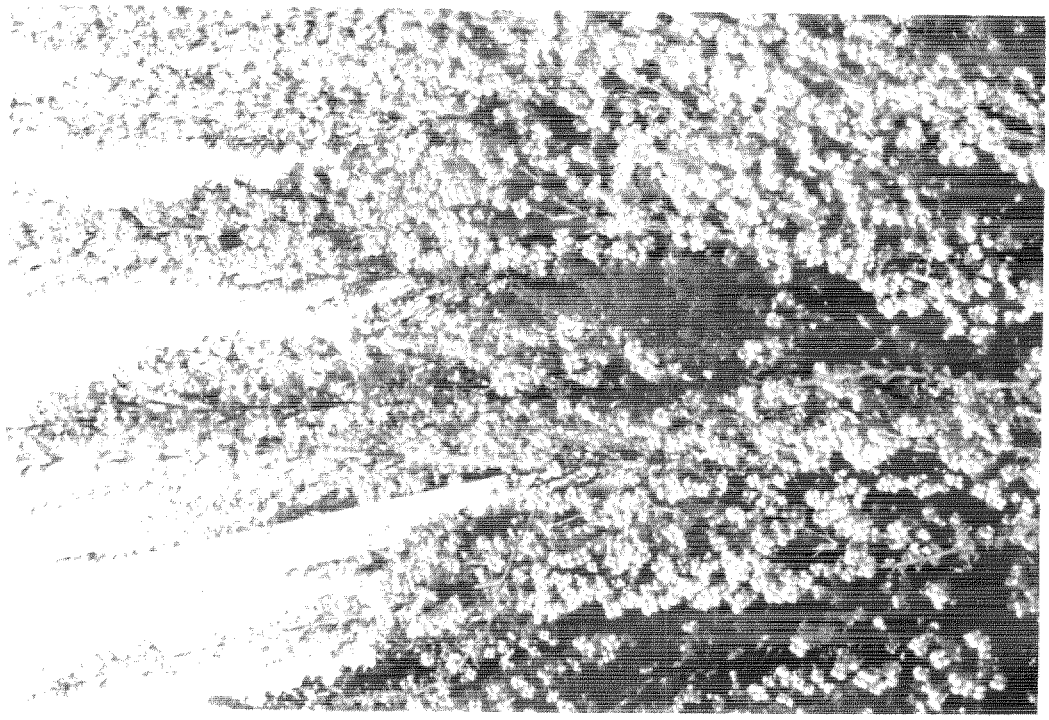
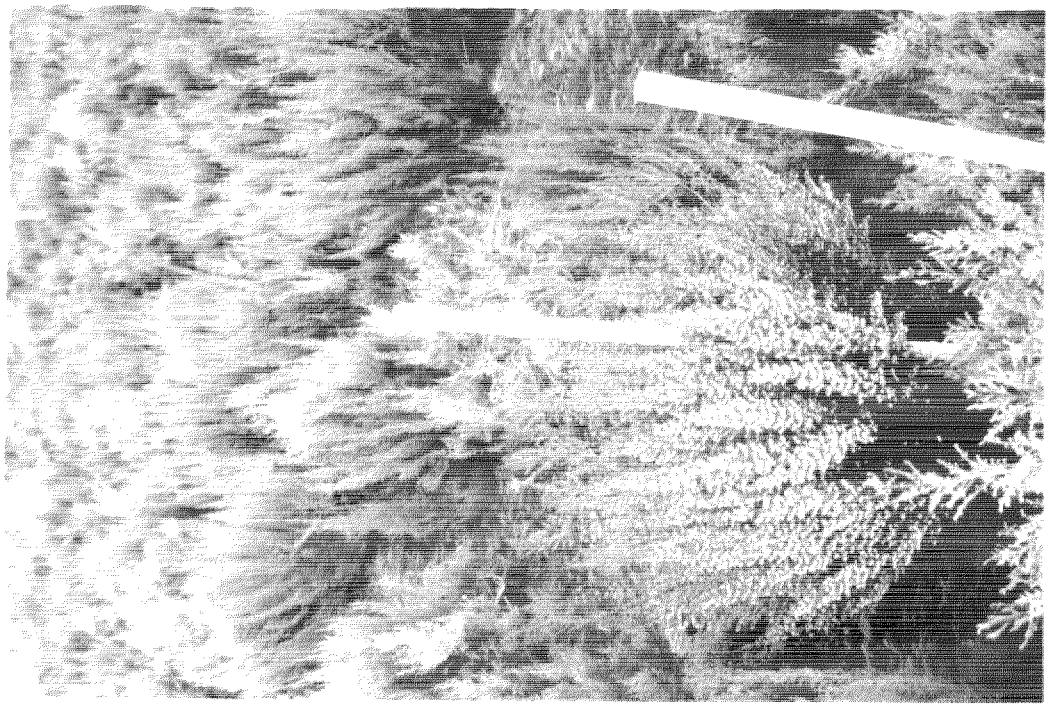

* * * * *